United States Patent [19]

Yamamura et al.

[11] 4,274,005
[45] Jun. 16, 1981

[54] X-RAY APPARATUS FOR COMPUTED TOMOGRAPHY SCANNER

[75] Inventors: Toshio Yamamura; Takeshi Muraki, both of Yokohama; Heihachi Miura, Kawasaki, all of Japan

[73] Assignee: Tokyo Shibaura Denki Kabushiki Kaisha, Kawasaki, Japan

[21] Appl. No.: 66,765

[22] Filed: Aug. 14, 1979

[30] Foreign Application Priority Data

Sep. 29, 1978 [JP] Japan .................................. 53-119205

[51] Int. Cl.³ ............................................ G03B 41/16
[52] U.S. Cl. ................................ 250/445 T; 250/419; 250/402
[58] Field of Search ..................... 250/445 T, 419, 430

[56] References Cited

U.S. PATENT DOCUMENTS

| | | | |
|---|---|---|---|
| 1,896,206 | 2/1933 | Smith | 250/419 |
| 4,031,395 | 6/1977 | Le May | 250/445 T |
| 4,048,503 | 9/1977 | Taylor | 250/445 T |
| 4,066,901 | 1/1978 | Seppi | 250/445 T |
| 4,126,786 | 11/1978 | Le May et al. | 250/445 T |
| 4,153,842 | 5/1979 | Rohmfeld | 250/445 T |

Primary Examiner—Craig E. Church
Attorney, Agent, or Firm—Cushman, Darby & Cushman

[57] ABSTRACT

In an X-ray apparatus for a computed tomography scanner, a plurality of combined X-ray tube segments are arranged round the central axis of the apparatus on which a subject to be examined is disposed. The X-ray tube segments each include a large number of electron beam generating means to produce an electron beam, a strip-like target having a surface against which the electron beam strikes and extending along a circular arc round the central axis, and an envelope containing these components. Along the surfaces of the X-ray tube segments facing the central axis lie a large number of X-ray detector elements to detect doses of fan-shaped X-ray beams emitted from the target and transmitted through the to-be-examined subject. The electron beam generating means successively produce electron beams, and fan-shaped X-ray beams are applied one after another to the subject from around the same.

24 Claims, 19 Drawing Figures

X-RAY APPARATUS FOR COMPUTED TOMOGRAPHY SCANNER

This invention relates to an X-ray apparatus, more specifically to an X-ray apparatus for a computed tomography scanner, capable of reconstructing x-ray tomographic images of a subject or body to be examined.

Appearing in U.S. Pat. No. 3,983,398, for example, a computed tomography scanner is generally known as an apparatus to reconstruct a cross-sectional image of a subject or body to be examined by detecting by means of an X-ray detector a transmission value of X-ray beams transmitted through a region of interest of the body and processing the value by means of a computer. In such computed tomography scanner, the X-ray beams need be radiated toward the to-be-examined body from various directions. Heretofore, there has been employed a means for rotating an X-ray tube round the body to be examined in order to radiate the X-ray beams from around the body. The problem with the computed tomography scanner using such rotating means lies in that scanning for the reconstruction of a tomographic image requires more than several seconds, which makes it difficult to photograph a region of interest of a subject that moves incessantly, such as the heart of a human body, missing the possibility of reproducing a clear tomographic image. An X-ray apparatus overcoming this problem is disclosed in Laid-Open Publication No. 50,186/77 published on Apr. 21, 1977 with the respect to Japanese Patent Application No. 12,436/76 to which priority is claimed on the basis of British Patent Applications Nos. 42,869/75, 3,614/76, 8,646/76 and 30,984/76. The X-ray apparatus appearing in this Laid-Open Publication is provided with a doughnut-shaped X-ray tube having an elongate target, and has its electron beam emitting point moved in a mechanical or electrical manner, a subject to be examined being disposed in the central region of the apparatus. Since the position of the electron beam emitting point faced to the target is changed in turn and an X-ray beam generating point on the target shifts its position correspondingly, so X-ray beams may be radiated from around the body or subject to be examined.

According to the X-ray apparatus disclosed in the aforementioned Publication, the to-be-examined body can securely be scanned at a high speed, and the tomographic image may be reconstructed in a shorter time. However, the subject to be examined is relatively bulky, so that the X-ray tube must be large in size, requiring, for example, a doughnut-shaped envelope with a diameter of 2 m. It is very difficult to manufacture such type of X-ray tube, and besides it is not easy to incorporate or remove such a large tube into or from a computed tomography scanner. Moreover, only a partial defect in the X-ray tube would require that the whole body of the X-ray tube be replaced by a new one.

The object of this invention is to provide an X-ray apparatus for a computed tomography scanner that is easy to manufacture, assemble and replace, and is capable of scanning a subject to be examined at a high speed.

According to this invention, there is provided an X-ray apparatus for a computed tomography scanner, having a central axis thereof, comprising two or more X-ray tube segments combinedly arranged along a circular arc around the central axis, each X-ray tube segment including at least one electron beam generating means to produce an electron beam, a target having a surface for emitting a X-ray beam from one of the focal points struck by the electron beam toward the central axis, said target being extended substantially along a circular arc around the central axis, and an airtight envelope containing the electron beam generating means and the target, and an X-ray detecting means composed of a plurality of detector elements for detecting the X-ray beam emitted from the X-ray tube segment and transmitted through a central region including the central axis.

This invention can be more fully understood from the following detailed description when taken in conjunction with the accompanying drawings, in which.

Figure 1:
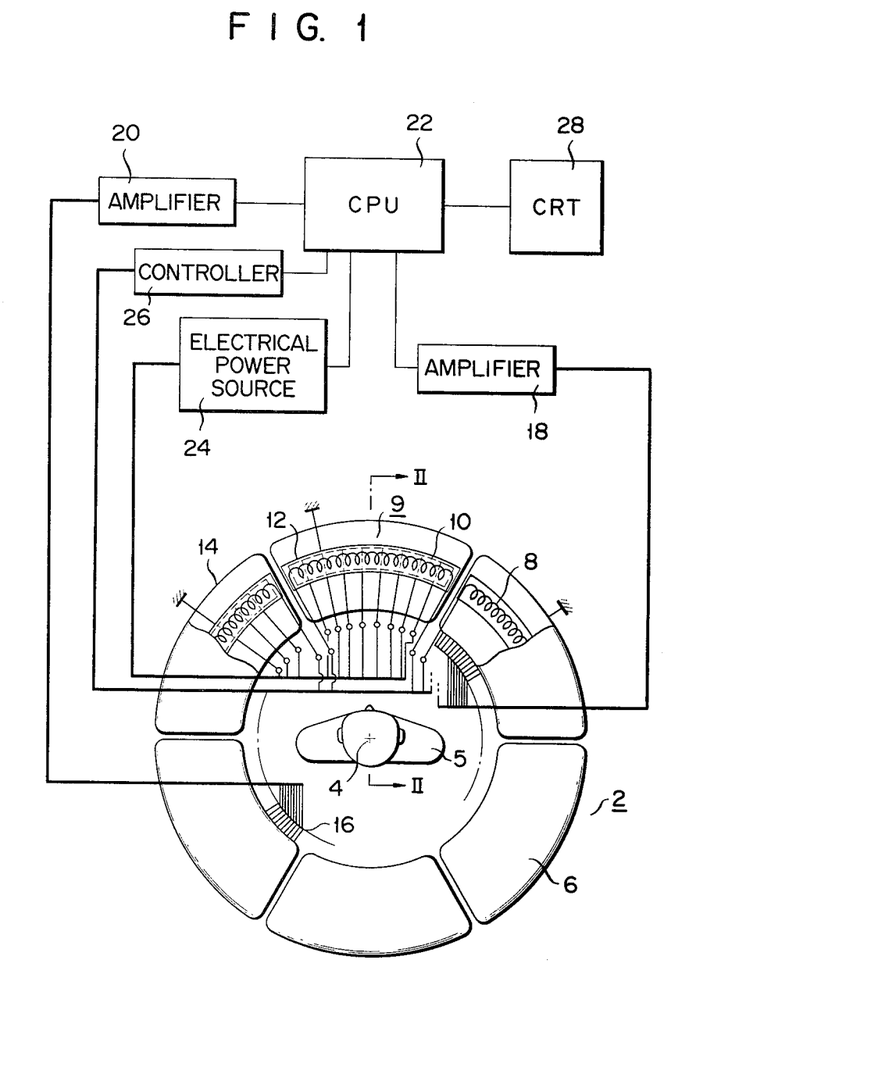
FIG. 1 is a schematic block diagram of a computed tomography scanner with an X-ray apparatus according to one embodiment of this invention.

FIG. 1 is a schematic view of a computed tomography scanner with an X-ray apparatus 2 according to this invention, in which a subject or body 5 to be examined is located in a central position 4 of the X-ray apparatus 2 which is doughnut-shaped as illustrated. The X-ray apparatus 2 is composed of several, e.g. six, X-ray tube segments 6 which are combined into a doughnut-shaped entire body. As described later in detail, each of these segments 6 is formed of a plurality of electron beam generating means 9, an anode target 12 to produce X-rays from a focal point to which an electron beam is applied, and a vacuum envelope 14 containing these components. Each of the electron beam generating means 9 is formed of an elongate cathode 8 to produce electron beams and a control grid 10 disposed correspondingly to the cathode 8 and allowing the electron beams from the cathode 8 to be emitted. A collimator (not shown in FIG. 1) is attached to a side of the X-ray tube segment 6 facing the subject 5. An X-ray beam passed through the collimator is fan-shaped and is exposed to the subject 5. Further, the X-ray apparatus 2 is provided with an X-ray detector unit 16 consisting of a plurality of reference X-ray detectors for directly measuring a dose of X-rays emitted from the target 12 and a plurality of main X-ray detectors for measuring a dose of X-rays transmitted through the subject 5, the X-ray detector unit 16 being arranged along the inner periphery of the X-ray apparatus 2.

The reference and main X-ray detectors of the X-ray detector unit 16 are connected to a CPU (central processing unit) 22 through amplifiers 18 and 20, respectively, and detected signals are supplied to the CPU 22. The cathode 8 of each X-ray tube segment 6 is connected to an electric power source 24 which supplies the cathode 8 with electric power. The power source 24 is connected to the CPU 22, which controls the power supply from the power source 24 to the cathode 8. A controller 26, which controls the control grids 10 of all the X-ray tube segments 6, is connected to the CPU 22. The controller 26 controls the respective control grids 10 so as to on-voltage temporarily, the control grids 10 being successively kept at cut-off voltage, and then restore them to cut-off voltage again. The CPU 22 is connected further to a cathode ray tube (CRT) 28.

A cross-sectional image of the body 5 to be examined by the above-mentioned computed tomography apparatus is obtained as follows. Prior to photographing, the cathodes 8 of the X-ray tube segments 6 are supplied with electric power from the electric power source 24 in response to a command from the CPU 22, and are all heated simultaneously. In this case, the targets 12 are at the ground potential, the cathodes 8 are maintained at a high negative potential, and the control grids 10 are held at a negative cut-off potential as compared with the cathodes 8 in course of preparation for the photographing. Then, in the photographing, the controller 26 is operated in accordance with a command from the CPU 22 to release the cut-off state of the control grids 10 successively from the one located at the end of the first X-ray tube segment 6, and thereafter to restore the control grids 10 severally to the cut-off state. Thus, an electron beam is emitted from each cathode 8 and hits against the anode target 12, and a X-ray beam is radiated from a corresponding point of the target 12 struck by the electron beam. When all the control grids 10 of the first X-ray tube segment 6 have been driven from one end to the other, the control grids 10 of the second X-ray tube segment 6 adjacent to the first one are driven in the same manner. Thus, fan-shaped X-ray beams are emitted successively toward the to-be-examined body 5. Doses of X-rays at various X-ray emitting points on the target 12 are detected by the reference X-ray detectors, and applied as electric signals to the CPU 22 via the amplifier 18. These electric signals are used for electrical correction of unevenness, if any, in doses of X-rays at the several X-ray emitting points. A dose of X-rays transmitted through the body 5 is detected by a number of main X-ray detectors arranged on the opposite side of the body 5 to the target 12 from which the X-ray beam is radiated, and is supplied as an electric signal to the CPU 22 through the amplifier 20. Thus, practical electron beam scanning is achieved by the electrical control, X-rays are successively emitted at regular intervals to cover the whole periphery of the body 5, and a dose of X-rays and an X-ray signal are detected with every such emission. The detected doses and signals are arithmetically processed by the CPU 22, whereby an X-ray tomographic image can be reconstructed on the CRT 28, for example.

For the photographing of cross-sectional images of the trunk of a human body, for example, the doughnut-shaped X-ray apparatus 2 formed of a plurality of X-ray tube segments 6 may have outside and inside diameters of 1.8 m and 1.5 m, respectively. If the electron beam generating means 9 of each X-ray tube segment 6 has 50 control grids arranged at regular intervals, X-rays are successively emitted from 300 (50×6) positions on the target 12 for the entire periphery of the X-ray apparatus 2. Accordingly, 300 reference X-ray detectors and 500 to 1,000 main X-ray detectors are arranged at regular intervals over the whole periphery of the apparatus 2. If the bias voltage of each of the 300 control grids 10 is controlled in 200 μsec, photographing of one cross-sectional image may be accomplished in 60 msec (200 μsec×300). It is to be understood that these figures are given as an example and that the time required for the photographing may be further reduced.

If the anode voltage and the anode current between the anode target and the cathode are 100 kV and 1A (pulse width 100 μsec) respectively, the amount of heat applied to the target of one X-ray tube segment is approximately 500 J, which may be fully radiated by directly liquid-cooling a metal base to which the anode target is fixed.

Figure 6:
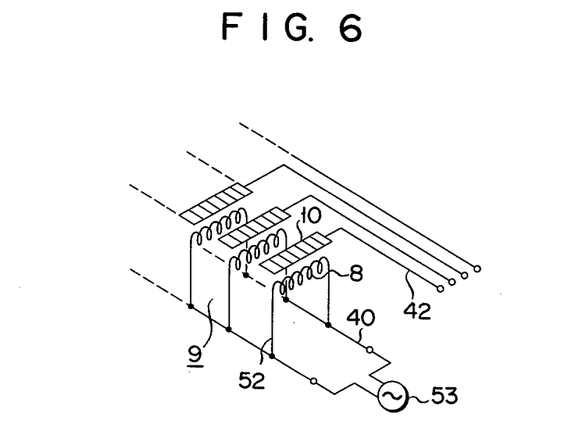
FIG. 6 is a schematic wiring diagram showing the electron beam generating means of FIGS. 4 and 5.

Referring now to the drawings of FIGS. 2 to 8, there will be described in detail the construction of the X-ray apparatus 2. As already mentioned, each X-ray tube segment 6 is one of e.g. six radially divided equal parts of the doughnut-shaped X-ray apparatus 2. The vacuum envelope 14 of the segment 6 is formed of material highly permeable to X-rays, such as glass and ceramics. The opening end of the envelope 14 is sealed airtightly with an anode base metal 32 with high heat conductivity (e.g. copper) by means of a sealing metal 30 such as Kovar. Inside the other end of the vacuum envelope 14, the electron beam generating means 9 composed of the cathodes 8 and control grids 10 and held by a supporting member 34, and a reduced-diameter neck portion 36 formed integrally with the main body of the envelope 14 and protruding therefrom and an exhaust pipe 38 are formed at the other end. The neck portion 36 is airtightly penetrated by a pair of cathode lead wires 40 and a plurality of control grid lead wires 42. As shown in detail in FIGS. 4 and 5, the electron beam generating means 9 each include a focusing electrode 46 with an elongate focusing slot 44 for focusing electron beams emitted from the cathode 8, the cathode 8 formed of a spiral tungsten filament stretched inside the electrode 46 and elongated radially with respect to the central axis 4, and the control grid 10 formed of a plurality of wires so arranged as to control the emission of electron beams from the cathode 8. These electron beam generating means 9, 50 in number, are arranged at regular intervals with insulators 48 such as ceramics between in each X-ray tube segment, facing the arcuate anode target 12. The control grid 10 is welded directly to the focusing electrode 46 for the same electric potential, and is connected to its corresponding control grid lead wire 42. The grid 10 and the focusing electrode 46 may, however, be electrically insulated so as to have different potentials. Each cathode 8 is insulated from its corresponding focusing electrode 46 by means of an insulating pipe 50 penetrating the focusing electrode 46, and is parallel-connected with the lead wires 40 by means of supporting rods 52, with both sides supported respectively by the rods 52. As shown in FIG. 6, the cathode 8 is disposed correspondingly to each of the control grids 10, and a control voltage may be supplied independently to each control grid 10. All the cathodes 8 are connected in parallel with a power source 24, and ignited at the same time.

Figure 2:
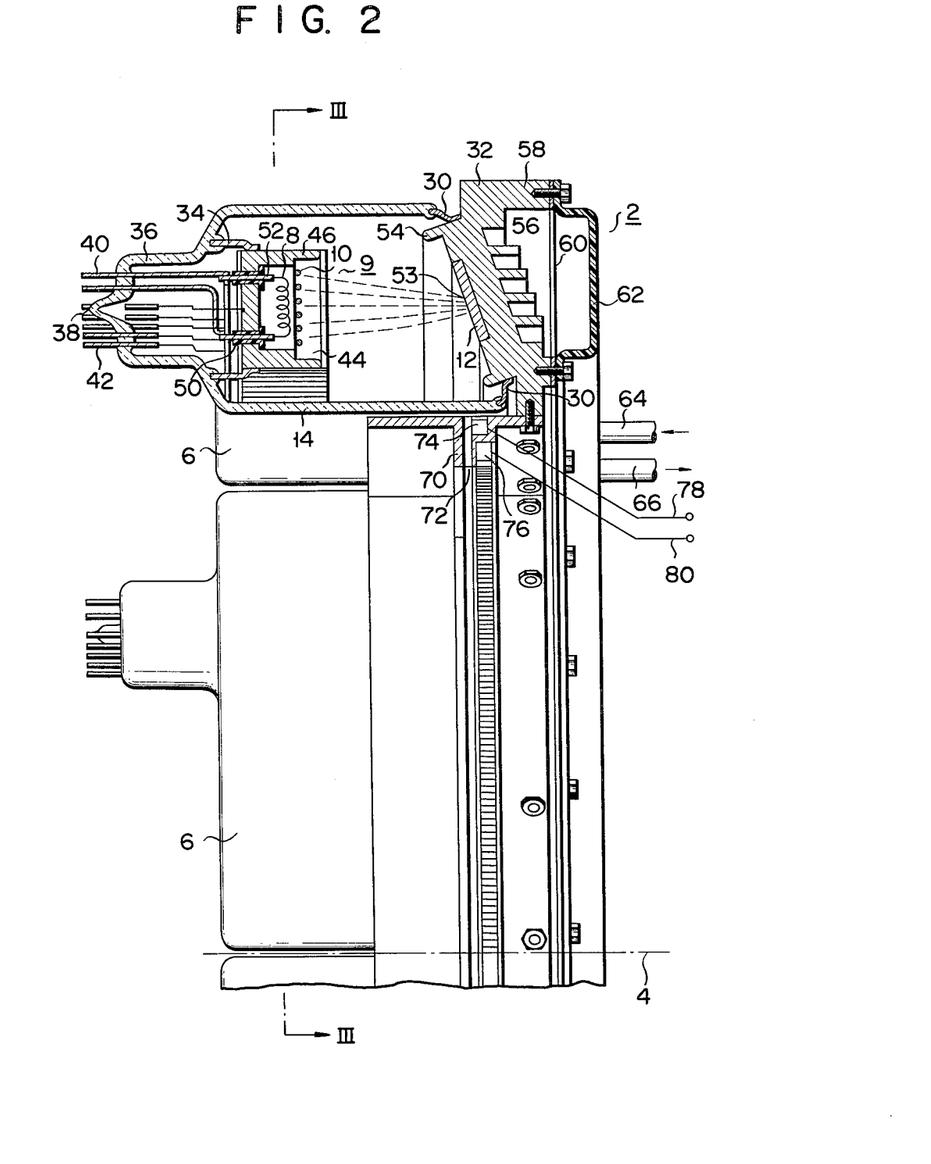
FIG. 2 is a schematic sectional view of the X-ray apparatus as taken along line II—II of FIG. 1.
Figure 3:
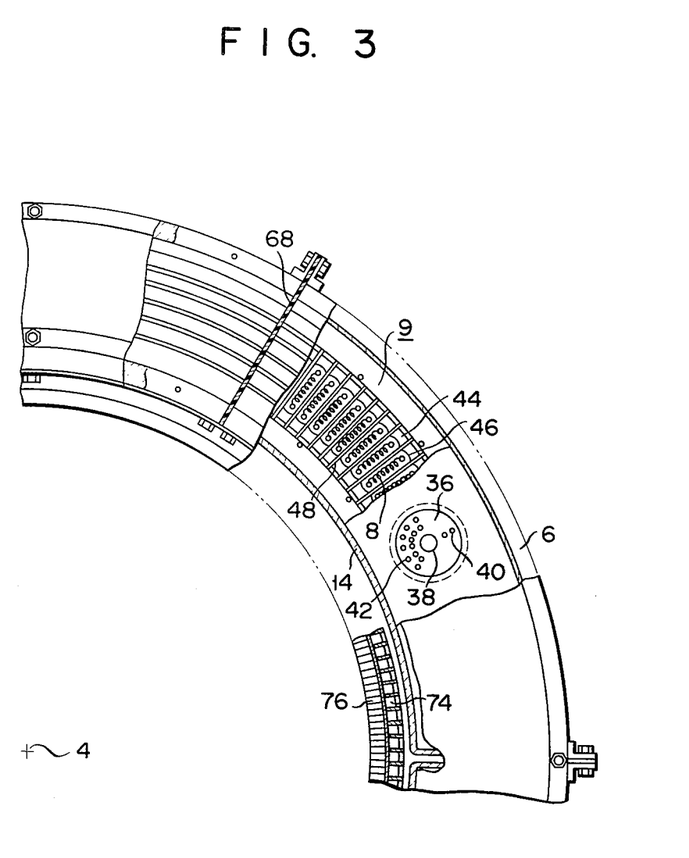
FIG. 3 is a schematic partial sectional view of the X-ray apparatus including partial sections as taken along lines III—III of FIG. 2.
Figure 4:
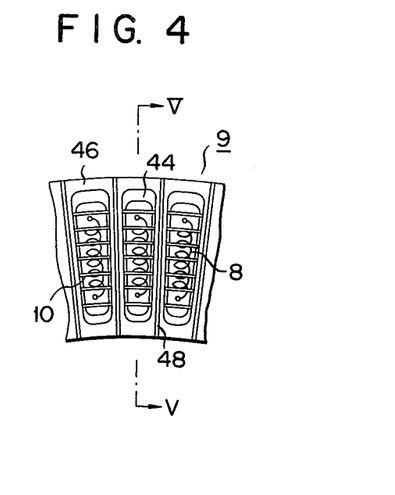
FIGS. 4 and 5 are a front view and a sectional view as taken along line V—V thereof, respectively, schematically showing electron beam generating means incorporated into an X-ray tube segment of the X-ray apparatus of FIG. 2.
Figure 5:
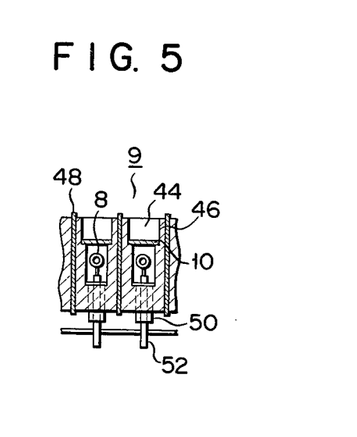

The X-ray emitting target 12 made of tungsten or some other heavy metal is embedded in a surface of the anode base metal 32 facing the cathode 8, the plane of the target having a tilt relative to the central axis 4. An electron beam emitted from the cathode 8 is projected substantially in parallel with the central axis 4 to form an electron beam impact region or X-ray actual focal point 53 on the target 12. The actual focal point is a rectangular form elongated radially with respect to the central axis 4. However, an effective focal point obtained by viewing the rectangular actual focal point through the collimator is apparently small, and such small effective focal point may be regarded as a source of an X-ray beam 55 to be applied to the to-be-examined subject 5. At each side of the target surface or inner surface of the base metal 32 is provided a flange 54 to protect the joint portion between the sealing metal 30 and the envelope 14 against electron impact, while arcuate radiating fins 56 are formed on the outer surface of the base metal 32. Respectively at both ends of the outer surface of the base metal 32 are flanges 58 protruding outward. A liquid-cooling jacket 62 is screwed to the flanges 58 through a packing 60 of rubber or the like. The liquid-cooling jacket 62, having an annular shape, is singly fitted on all of the six X-ray tube segments after they are put together. The liquid-cooling jacket 62 is fitted with pipes 64 and 66 for introducing and discharging cooling water into and from a space between the liquid-cooling jacket and the outer surface of the base metal 32. Each two adjacent X-ray tube segments are coupled liquid-tightly to each other with a rubber packing 68 interposed between their respective base metals. Thus, a circulating path for circulating the coolant throughout the whole circumference is defined along the outer surfaces of the base metals of all the X-ray tube segments. In order to improve the cooling efficiency, the coolant is circulated in a direction opposite to the electron beam scanning direction. The pipes 64 and 66, therefore, are attached to positions corresponding to the respective positions of the cathodes for the first and last emissions of the X-ray beam 55 in one operation of the X-ray apparatus 2. That is, referring to the hour hand of a clock, if the X-ray beam 55 is allowed first to be emitted from a position corresponding to nearly 1:00, and the X-ray beam emitting position is shifted in the clockwise direction for scanning, then the coolant is circulated in the opposite direction to the clockwise direction. To attain this, the introduction pipe 64 and the discharge pipe 66 are attached respectively to positions just ahead of and behind the position corresponding to 1:00, and a partition is provided in close vicinity to the position of 1:00 inside the jacket. By doing this, the position subject to the electron beam impact and generation of heat may be cooled always by the lowest-temperature portion of the coolant.

Figure 7:
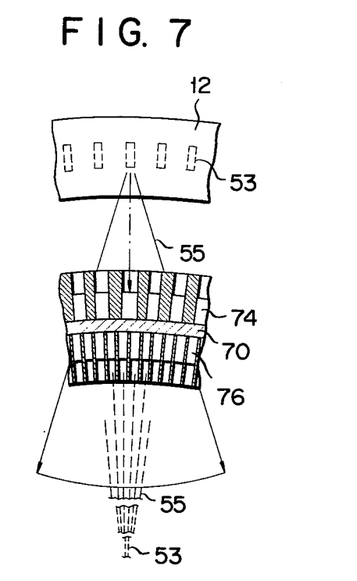
FIGS. 7 and 8 are schematic sectional views showing the relative locations of a collimator and X-ray detectors incorporated into the X-ray tube segment of the X-ray apparatus of FIG. 2.
Figure 8:
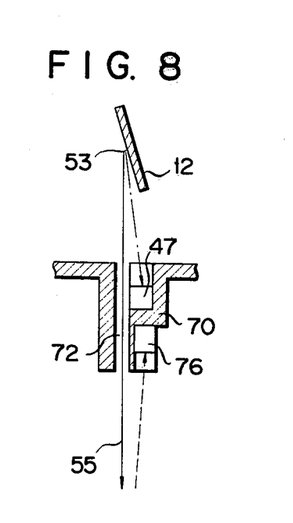

A collimator 70, which is formed of an X-ray screening metal plate such as lead, is provided with a slit 72 for the passage of the X-ray beam 55. The X-ray beam 55 passed through the slit 72 is rectified into a fan-shaped beam. As shown in FIGS. 2, 3 and 7, a large number of reference X-ray detectors 74 with their X-ray input surfaces directed toward the target 12, as well as a number of main X-ray detectors 76 with their X-ray input surfaces directed toward the central axis 4, are arranged in the vicinity of the slit 72. The reference X-ray detectors 74, which tend directly to detect X-rays from the target 12 to provide reference signals, are arranged correspondingly to the X-ray focal points 53 formed on the target by electron beams from their corresponding cathodes 8. 50 reference X-ray detectors are provided for each X-ray tube segment 6. Each reference X-ray detector 74 is connected with a lead wire 78 through which the signals are taken out. The main X-ray detectors 76, 150 in number, are arranged at regular intervals along the inner periphery of each X-ray tube segment 6, tending to receive X-rays emitted from the target 12 of the X-ray tube segment 6 facing thereto and transmitted through the subject 5. Thus, a total of 900 main X-ray detectors are disposed over the whole inner periphery of the X-ray apparatus 2. As shown in FIGS. 2 and 8, the reference and main X-ray detectors 74 and 76 are isolated by the X-ray screening metal plate consituting the collimator 70. The collimator 70 and the X-ray detector unit 16 including the reference and main X-ray detectors 74 and 76 are constructed in a body, and fixed to the flange 54 on the inner side of the base metal 32 of each X-ray tube segment 6 for accurate location. Naturally, instead of being fixed to the X-ray tube segment 6, these components may be disposed separately. In this invention, the group of these detector elements are defined as the X-ray detector unit 16 even in a case where both or one of the reference and main detectors 74 and 76 are arranged in the vicinity of the target 12.

The X-ray tube segments 6 are put together into a doughnut-shaped body by suitable fixing means. These X-ray tube segments 6, which may be housed in a suitable casing filled with insulating oil, are independently removably fixed, in any case. Accordingly, if any one of the X-ray tube segments 6 is found defective, it may be replaced singly. Although the joint between each two adjacent X-ray tube segments 6 may form a discontinuous region where the X-ray emitting points or focal points 53 are missed, such discontinuity can be limited to a distance corresponding at most to one focal point, hardly exerting any bad influence upon the quality of resultant X-ray tomographic images.

The X-ray apparatus 2 of this invention as described above may be produced in commercial quantity since the maximum length of each X-ray tube segment can be limited to approximately 80 cm. Moreover, the individual X-ray tube segments can easily be attached and detached, so that the assembly and handling of the apparatus may be facilitated and any defective X-ray tube segment may be replaced independently. Furthermore, by fixing the collimator and the X-ray detector unit separately to the X-ray tube segment, they may be located accurately, and their positions may substantially be prevented from being shifted.

Referring now to FIGS. 9 to 17, there will be described a modification of the X-ray apparatus of this invention.

Figure 9:
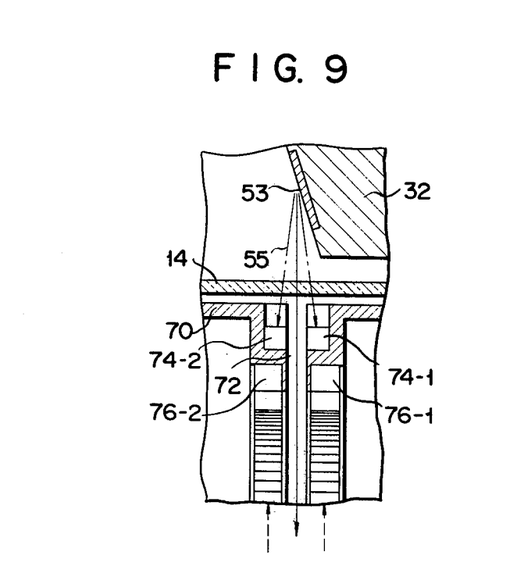
FIGS. 9, 10 and 11 are schematic sectional views showing a modification of the relative locations of the collimator and X-ray detectors as shown in FIGS. 7 and 8, and an alternative embodiment.

In an example of FIG. 9, reference X-ray detectors 74-1 and 74-2 and main X-ray detectors 76-1 and 76-2 are closely arranged on both sides of an X-ray beam path or the slit 72, respectively. With thus arranged two types of X-ray detectors, two close cross-sectional images may be reproduced by one scanning operation. Two close fan-shaped X-ray beams may be radiated simultaneously toward the to-be-examined body 5 respectively through two slits provided for the collimator so that X-ray signals for the two cross-sectional images can be obtained severally by means of the X-ray detector unit 16.

Figure 10:
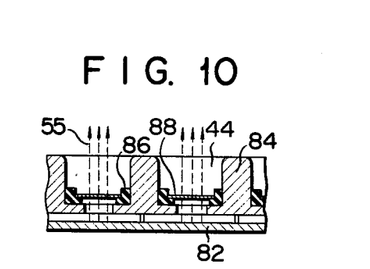
Figure 11:
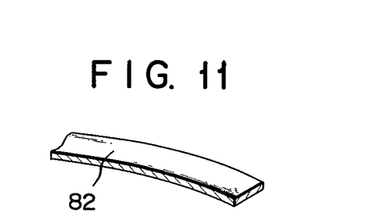

In another example of the electron beam generating means 9 as shown in FIG. 10, an elongate flat cathode 82 as shown in FIG. 11 and an elongate focusing electrode 84 with a plurality of focusing slots 44 bored therein extend inside the vacuum envelope of one X-ray tube segment from one end thereof to the other, the cathode 82 and the focusing electrode 84 being connected at the same potential. Inside each focusing slot 44 is a control grid 88 fixed on an insulator 86 and connected to its corresponding lead wire. The flat cathode 82 may be of a directly heated type such as pure tungsten and thorium-turngstem, or of an indirectly heated type. This electron beam generating means 9 is easier to assemble because the electrodes except the control grid 88 are formed in a block.

Figure 12:
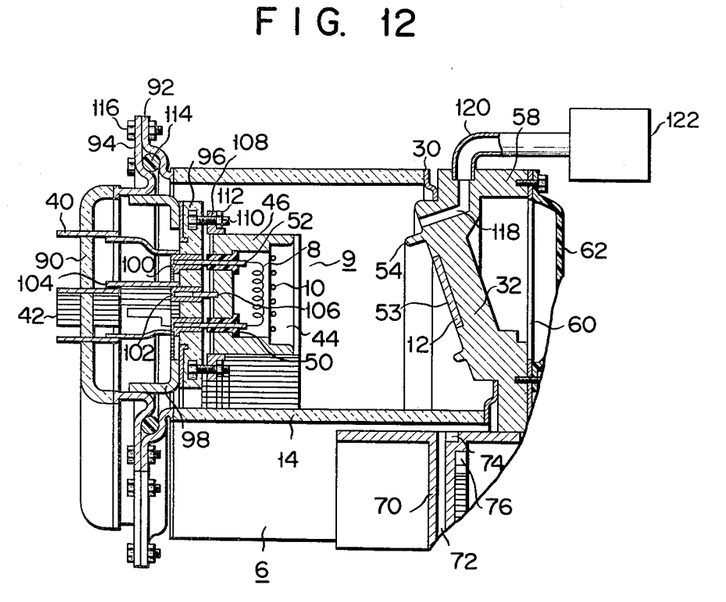
FIG. 12 is a sectional view schematically showing a modification of the X-ray tube segment of the X-ray apparatus of the invention.
Figure 13:
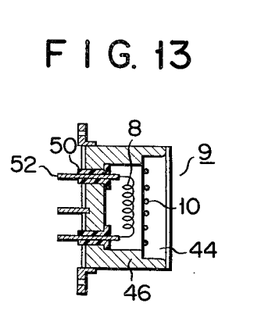
FIGS. 13 and 14 are a sectional view and a front view of electron beam generating means as shown in FIG. 12, respectively.
Figure 14:
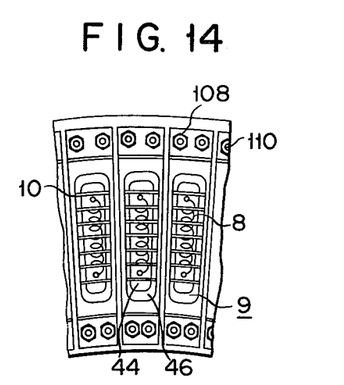

The X-ray tube segment 6 according to an alternative embodiment as shown in FIGS. 12 to 14 is so constructed that each individual electron beam generating means 9 can be replaced independently, and that the direction of electron beam can be adjusted minutely. Further, the X-ray tube segment 6 has its vacuum envelope 14 separable. That is, the vacuum envelope 14 formed of ceramics or other insulating material has two openings, one of which, as already described, is fitted with the base metal 32. In this embodiment, the other opening of the envelope 14 is airtightly fitted with a cover portion 90 by means of flanges 92 and 94 that are formed on the envelope 14 and the cover portion 90 respectively. The cover portion 90 is fixed by an insulating base plate 96 by means of a metal fitting 98. The insulating base plate 96 is provided with connecting terminal pins 100 and 102 for the cathode and control grid, while the lead wires 40 and 42 are provided for the cover portion 90. The control grid terminal pin 102 is connected to the lead wire 42 by means of a strip line 104. On the insulating base plate 96 are 50 electron beam generating means 9 removably fixed at regular intervals. Namely, the terminal pins 100 and 102, as shown in FIG. 12, are provided with insertion holes in which the cathode supporting rods 52 and lead wires 106 for the control grid and focusing electrode are inserted, respectively. Metal fittings 108 are screwed on screws 110 rotatably attached to the base plate 96, and are fixed securely by fixing nuts 112. The screws 110 are provided for the four corners of each electron beam generating means 9. The inclination of each electron beam generating means 9 relative to the base plate 96 may freely be regulated by adjusting the screws 110. The flanges 92 and 94 fixed to part of the vacuum envelope are fixed tight by means of screws 116 through vacuum ring gaskets 114. The anode base metal 32 is provided with an exhaust path 118, which is fitted with an exhaust pipe 120. A vacuum pump 122 maintains a vacuum inside the vacuum envelope. If the focal points of X-ray beams are subject to unevenness, the screws 116 are unfastened to remove the cover portion 90 after stopping the vacuum pump, and the X-ray beam focal points are located to accurate positions by finely adjusting the screws 110. Further, in the X-ray tube segment 6 of this embodiment, if a cathode suffers disconnection or defective electron emission, it may independently be replace for the resumption of operation. Moreover, after the positions of the X-ray focal points are located properly, the flanges 92 and 94 of the vacuum envelope 14 and the cover portion 90 may be airtightly welded together.

Figure 15:
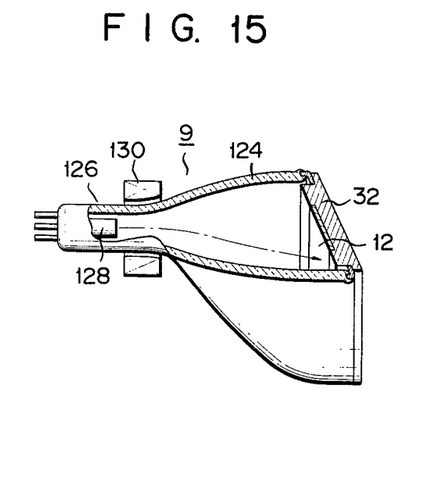
FIG. 15 is a partial sectional view schematically showing another modification of the X-ray tube segment of the X-ray apparatus of the invention.
Figure 16:
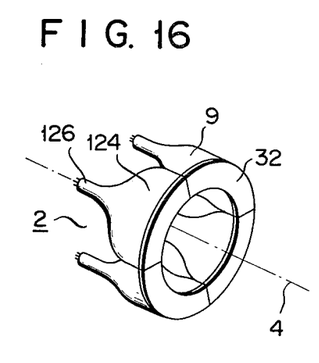
FIG. 16 is a perspective view of the X-ray apparatus of the invention combining the X-ray tube segments as shown in FIG. 15.
Figure 17:
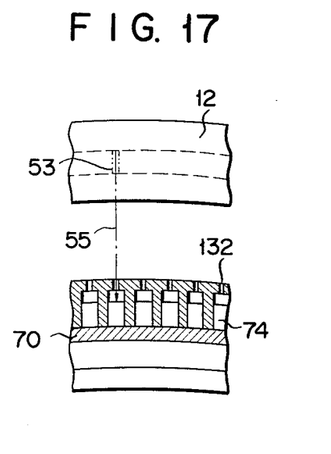
FIG. 17 is a sectional view schematically showing a modification of the collimator incorporated into the X-ray tube segment of FIG. 15.

In an embodiment as shown in FIGS. 15 to 17, each X-ray tube segment 6 is so constructed that X-ray beams are emitted from a number of focal points on the target 12 to scan the to-be-examined subject 5 by deflection scanning or the target 12 with a single electron beam. The X-ray tube segment 6 includes the inclined anode base metal 32 and the elongate target 12. The vacuum envelope 14 has a curved large-diameter portion 124 to hold the target 12 and a small-diameter neck portion 126 which contains an electron gun 128 to produce electron beams. An electromagnetic deflecting coil 130 for electron beam deflection scanning control is located around the outer periphery of the neck portion 126 ahead of the electron gun 128. The electron gun 128 has a control grid (not shown in FIG. 15). The deflection scanning may be performed by using an electrostatic deflecting device instead of the electromagnetic deflecting coil 130. As shown in FIG. 17, each of the reference X-ray detectors 74 attached to the collimator 70 is provided with an X-ray window 132 to admit only X-rays emitted from an electron beam impact position corresponding to the relevant detector 74. The use of the X-ray windows 132 makes it possible to detect accurately the focal point form which an X-ray beam is emitted and a dose of X-rays at that point. The electron beams may be produced pulsatively or continuously to cause X-rays to be emitted from the targets 12 over the whole circumference of the X-ray apparatus 2.

Figure 18:
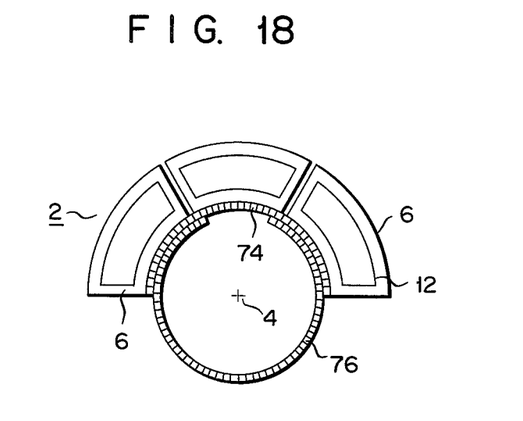
FIG. 18 is a schematic view of an X-ray apparatus according to another embodiment of the invention, in which the combination of X-ray tube segments is different from that of the apparatus of FIG. 1.

In the apparatus of this invention, the X-ray tube segments need not be arranged over the whole circumference of a circle round the central axis 4. However, to obtain a good tomography image, these segments may be preferably combined and arranged so as to cover an angular range of 180° or more round the central axis 4, as shown in FIG. 18. In this case, however, the main X-ray detectors 76 out of the X-ray detector unit 16 need be disposed also on the opposite side to the X-ray tube segments.

Figure 19:
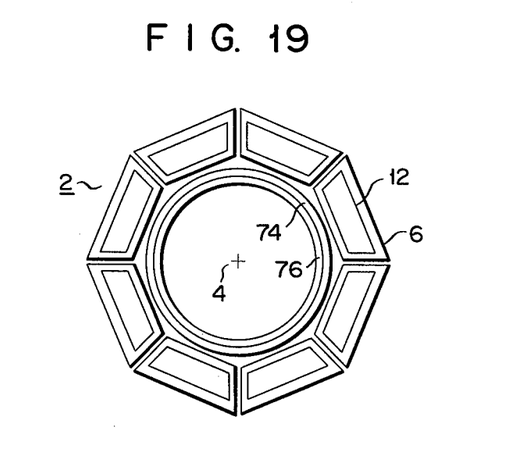
FIG. 19 is a schematic view of an X-ray apparatus according to still another embodiment of the invention, in which X-ray tube segments different in shape from the X-ray tube segments of FIG. 1 are combined.

Moreover, as shown in FIG. 19, the shape of each X-ray tube segment 6 may resemble that of a side of a polygon so that a substantially doughtnut-shaped X-ray apparatus may be formed. In this case, the target 12, electron beam generating means 9 and vacuum envelope 14 need not have arcuate outward shapes, so that they may have rectilinear outlines, additionally facilitating the manufacture. However, the X-ray detectors 74 and 76 are to be arranged in a loop, and deviations in dose of rays and in angle attributable to the differences between the distances between the variedly located focal points and the central axis 4 should be corrected by means of the CPU.

As described above, the X-ray apparatus of this invention provides high economical efficiency, as well as facility for manufacture, assembly and handling, capable of sharply reducing the time required for the photographing of a cross-sectional image.

What is claimed is:

1. An X-ray apparatus for a computed tomography scanner which has a central axis thereof, comprising:
   two or more X-ray tube segments each segment including:
      means for generating electron beams,
      a target substantially extending along a circular arc around the central axis and adapted to be scanned by the electron beams to emit X-rays toward the central axis, and
      an airtight envelope receiving said electron beam generating means, said target having a metal member made of good heat conductive material and having an inner surface on which said target is supported and an outer surface,
   said X-ray tube segments combinedly arranged along the circular arc and each metal member of an X-ray tube segment being coupled to the adjacent metal members of adjacent X-ray tube segments to provide a circular array of such metal members;
   X-ray detecting means comprising a plurality of detector elements for detecting the X-ray beams transmitted through a central region including the central axis; and
   means for cooling said target including a liquid-cooling jacket fitted to said metal members defining a coolant circulating path between the outer surface of the circular array of the metal members and the liquid-cooling jacket.

2. An X-ray apparatus according to claim 1, wherein said X-ray tube segments are combinedly arranged along the whole circumference of a circle round the central axis.

3. An X-ray apparatus according to claim 1, wherein said X-ray tube segments are combinedly arranged along a circular arc covering a range of 180° round the central axis.

4. An X-ray apparatus according to claim 1, wherein each said X-ray tube segment coupled to another such segment or segments adjacent thereto is coupled in such a manner that said X-ray tube segment may be removed from said X-ray apparatus.

5. An X-ray apparatus according to claim 1, wherein the target of each said X-ray tube segment is so designed as to have its surface inclined relatively to the electron beam emitted from said electron beam generating means.

6. An X-ray apparatus according to claim 1, wherein said electron beam generating means includes a cathode having an elongate electron beam emitting surface, the longitudinal direction of which is substantially coincident with the radial direction as taken from the central axis.

7. An X-ray apparatus according to claim 1, wherein said electron beam generating means includes a cathode to produce electron beams, a control grid to control the production of the electron beams from said cathode, and a focusing electrode to focus the electron beams from said cathode.

8. An X-ray apparatus according to claim 1, wherein each said X-ray tube segment comprises a plurality of electron beam generating means, said means being coupled to one another through electrical insulators and having electron beam emitting surfaces thereof directed toward said target.

9. An X-ray apparatus according to claim 1, wherein each said electron beam generating means includes a cathode to produce electron beams, a control grid to control the production of the electron beams from said cathode corresponding thereto, and a focusing electrode to focus the electron beams from said cathode.

10. An X-ray apparatus according to claim 1, wherein each said X-ray tube segment comprises a plurality of electron beam generating means, said plurality of electron beam generating means including a common thermal cathode to produce electron beams from a number of portions on the surface thereof, each said electron beam generating means including a control grid to control the production of the electron beams and a focusing electrode to focus the electron beams, said control grid and focusing electrode being disposed correspondingly to each electron beam generating portion on said common thermal cathode.

11. An X-ray apparatus according to claim 1, wherein said target is in the form of an substantially elongated circular arc or a substantially straight line.

12. An X-ray apparatus according to claim 1, wherein the direction of a coolant flow through the coolant circulating path is opposite to that in which the electron beams are scanned.

13. An X-ray apparatus according to claim 1, further including heat radiation fins formed on the outer surface of said metal member to permit a coolant to flow therealong.

14. An X-ray apparatus according to claim 1, further comprising a collimator means for collimating the X-ray beam emitted from said target into a fanshaped beam.

15. An X-ray apparatus according to claim 1, wherein a pair of elements among said plurality of X-ray detector elements of said X-ray detecting means are located relatively close to each other and correspondingly to one of the X-ray emitting points on said target, and a path through which X-rays are passed is formed between said pair of elements.

16. An X-ray apparatus according to claim 1, wherein said plurality of detector elements of said X-ray detecting means are arranged substantially throughout the whole circumference of a circle round the central axis.

17. An X-ray apparatus according to claim 1, wherein each said X-ray tube segment includes an electron beam generating means, and said envelope is composed of a large-diameter portion to hold said elongate target and a small-diameter neck portion, said electron beam generating means being located inside said neck portion, and an electron beam deflecting means for the deflection scanning with the electron beam from said electron beam generating means along the surface of said target is disposed outside said envelope.

18. An X-ray apparatus according to claim 1, wherein said envelope is composed of a main body and a cover means separable from said main body, and is kept under vacuum during the operation of said X-ray apparatus.

19. An X-ray apparatus according to claim 1, wherein said target or electron beam generating means is disposed inside said envelope so as to be able to be removed from said envelope.

20. An X-ray apparatus according to claim 1, wherein said electron beam generating means is provided with an adjusting means for the fine adjustment of the direction of the electron beam.

21. An X-ray apparatus according to claim 1, wherein said plurality of detector elements of said X-ray detecting means are attached to the surfaces of said X-ray tube segments facing the central axis.

22. An X-ray apparatus according to claim 1, wherein said X-ray detecting means further includes a plurality of reference X-ray detector elements provided adjacent to the surface of said X-ray tube segment facing the central axis and adapted to detect a dose of X-rays directly projected thereon, for comparison with a detected value provided by said X-ray detector elements for detecting a dose of X-rays transmitted through the central area including the central axis corresponding to the X-ray emitting points on said target.

23. An X-ray apparatus according to claim 22, wherein said plurality of X-ray detector elements and reference X-ray detector elements are attached to the surfaces of said X-ray tube segments facing the central axis, each said reference X-ray detector element being located closer to said target than each said X-ray detector element is.

24. An X-ray apparatus according to claim 22, wherein said X-ray detecting means includes X-ray windows each disposed between each said reference X-ray detector element and each corresponding X-ray emitting point on said target, whereby X-rays from said X-ray emitting point only are admitted into said reference X-ray detector element.

* * * * *